United States Patent [19]

Sauer et al.

[11] Patent Number: 5,185,341
[45] Date of Patent: Feb. 9, 1993

[54] SUBSTITUTED 5-(PHENOXYALKANOYLAMINO)-URACIL COMPOUNDS, METHODS FOR MAKING SAME AND PHARMACEUTICAL COMPOSITIONS BASED ON SAME

[75] Inventors: Wolfgang Sauer, Dresden; Hans-Joachim Jänsch, Radebeul; Angelika Rostock, Dresden; Gottfried Faust, Radebeul; Christine Siegemund, Weinböhla; Dieter Lohmann, Radebeul; Reni Bartsch, Dresden, all of Fed. Rep. of Germany

[73] Assignee: Arzneimittelwerk Dresden GMBH, Radebeul, Fed. Rep. of Germany

[21] Appl. No.: 787,064

[22] Filed: Nov. 4, 1991

[30] Foreign Application Priority Data

Nov. 6, 1990 [DE] Fed. Rep. of Germany ....... 4035599

[51] Int. Cl.$^5$ .................. A61K 31/505; C07D 239/02
[52] U.S. Cl. ................................... 514/269; 514/274; 544/311
[58] Field of Search ................ 544/311, 312; 514/269, 514/274

[56] References Cited

U.S. PATENT DOCUMENTS

| | | | |
|---|---|---|---|
| 4,746,352 | 5/1988 | Wenper et al. | 544/312 |
| 4,908,368 | 3/1990 | Murase et al. | 544/311 |
| 4,912,109 | 3/1990 | Bapley et al. | 544/312 |

OTHER PUBLICATIONS

March, Advanced Org. Chem. 3rd Edition pp. 370-371, Reaction 0-54.
Susan J. Sara et al., Psychopharmacologia (Berl) 36, 59-66 (1974).
Hoffmann et al., Pharmazie 38 (1983) p. 869.
Von W. Raake et al., Arzheim-Forsch./Drug Res. 27(7), No. 1, 1977, p. 132.
Ordzhonikidze Antibiotic 24(1979) pp. 659-663.
Arzneim.-Forsch./Drug Res. 36 (11), 1568-1571 (1986).
C. Giurgea "Central Hypoxia Models and Correlations ...".
W. Hoffmann, et al. "Influence of AWD 23-15, A New Nootropic ...".
W. Hoffmann, et al. "Der Einfluss von Nootropica auf das ...".
R. Cumin, et al., Psychopharmacology (1982) 78: 104-111.
A. Rostock, et al., Meth and Find Exp. Clin. Pharmacol. 1989; 11(9).
W. Hoffmann, et al. Pharmazie 43 (1988), H. 4.
H. Kuribara, Japan J. Pharmacol. 48, 494 (988).
Biomed. Biochem. Acta 48 (1989) 2/3, pp. 247-250.

Primary Examiner—Cecilia Tsang
Attorney, Agent, or Firm—Michael J. Striker

[57] ABSTRACT

The substituted 5-(phenoxyalkanoylamino)-uracil compounds have the following formula I:

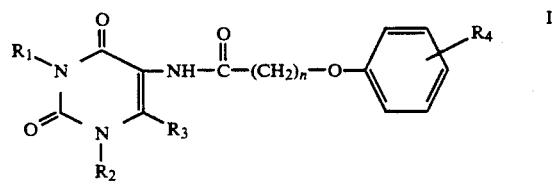

wherein $R_1$ and $R_2$ are each independently hydrogen; a branched or linear alkyl group having 1 to 6 carbon atoms; a branched or straight chain alkenyl or alkynyl group having 1 to 6 carbons atoms; a cycloalkyl group having from 3 to 7 carbon atoms or a cycloalkylmethyl group having a cycloalkyl residue of 3 to 7 carbon atoms; or a phenylalkyl group having an alkyl residue having from 1 to 3 carbon atoms and a phenyl residue, the phenyl residue being unsubstituted or having a halogen, methoxy, methyl or trifluoromethyl substituent; $R_3$ is a hydrogen, methyl or amino groups; $R_4$ is halogen, methoxy or methyl groups, and n is 1 or 2. Pharmaceutical compositions for treating cerebrovascular, neuronal-degenerative and senility-induced disorders associated with learning, memory and cognitive dysfunctions are described which contain a therapeutically effective amount of the substituted 5-(phenoxyalkanoylamino)-uracil in a pharmaceutically acceptable carrier.

9 Claims, No Drawings

SUBSTITUTED 5-(PHENOXYALKANOYLAMINO)-URACIL COMPOUNDS, METHODS FOR MAKING SAME AND PHARMACEUTICAL COMPOSITIONS BASED ON SAME

BACKGROUND OF THE INVENTION

The present invention relates to new substituted 5-(phenoxyalkanoylamino)-uracil compounds, methods of making them and their use as a therapeutic agent, particularly for the treatment of cerebral disorders and improvement of cerebral function.

The new substituted 5-(phenoxyalkanoylamino)-uracil compounds of the formula I, as shown in the invention summary below, according to the invention are characterized by a strong cerebroprotective action with simultaneously comparatively higher compatibility. Thus they can be used for prophylaxis and treatment of cerebrovascular, neuronal-degenerative and senility-induced disorders associated with learning, memory and cognitive dysfunctions.

The compound, 6-methyluracil, is known among other things from the literature(see German Patent Application File Number WP A61K/264 182.8 which corresponds to East German Patent DD 262 367). This compound has numerous biological effects. For example, it has an antibiotic action(Antibiotiki 24(1979) p.659) and can protect against radiation (Arzneimittelforschung 27(1977) p. 132)

In German Patent A 61 K/ 264 182.8 which corresponds to East German Patent DD 262 367 the use of 6-methyluracil as a nootropic drug is claimed. This nootropic drug has not been used in practice up to the present time. Nootropic drugs such as Piracetam and Meclofenoxate have been known for a long time in medical practice. There has been a need, however, to find materials which have an increased antiamnestic and antihypoxic action and thus are suitable for normalizing cerebral function under pathological conditions and to protect the cerebrum from oxygen deficiency.

SUMMARY OF THE INVENTION

It is an object of the present invention to provide new nootropically effective 5-(phenoxyalkanoylamino)-uracil compounds with valuable pharmaceutical properties and methods of making them.

According to the invention, the new substituted 5-(phenoxyalkanoylamino)-uracil compounds have the following formula I:

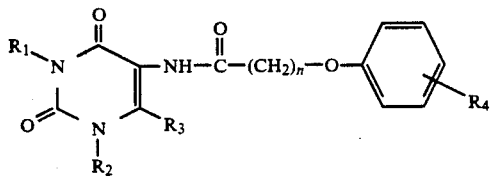

wherein $R_1$ and $R_2$ are each independently hydrogen, a branched or linear alkyl group of 1 to 6 carbon atoms, which can be substituted by an oxo- or hydroxy- group; a branched or linear alkenyl or alkynyl group having 1 to 6 carbons atoms, which can be substituted by an oxo-or hydroxy- group; a cycloalkyl or cycloalkyl-methyl group in which the cycloalkyl residue has from 3 to 7 carbon atoms; or a phenylalkyl group in which the alkyl residue has from 1 to 3 carbon atoms and the phenyl residue can have a halogen, methoxy, methyl or trifluoromethyl substituent group;

wherein $R_3$ is hydrogen, methyl or an amino group;

wherein $R_4$ is halogen, methoxy or methyl groups, and n is 1 or 2.

In one embodiment of the invention, the substituted 5-(phenoxyalkanoylamino)-uracil compound is
5-(p-chlorophenoxy-acetoamido)-1,4-dimethyluracil,
5-(p-chlorophenoxy-acetamido)-3,4-dimethyluracil,
5-(p-chlorophenoxy-acetamido)-1,3,4-trimethyluracil,
5-(p-chlorophenoxy-acetamido)-uracil, 3-benzyl-5-(p-chlorophenxoy-acetamido)-1,4-dimethyluracil,
4-methyl-5-(p-methoxyphenoxy-acetamido)-uracil,
4-methyl-5-(p-methylphenoxy-acetamido)-uracil,
5-(p-chlorophenoxy-acetamido)-4-methyluracil,
5-(p-chlorophenoxy-β-propionamido)-4-methyluracil,
5-(p-chlorophenoxy-β-propionamido)-1,3,4-trimethyluracil, 5-(p-chlorophenoxy-β-propionamido)-uracil hydrate, 5-(p-chlorophenoxy-acetamido)-4-methyluracil or 4-amino-5-(p-chlorophenoxy-acetamido)-1,3-dimethyluracil.

In another preferred embodiment of the invention the substituted 5-(phenoxyalkanoylamino)-uracil compound is 5-(p-chlorophenoxy-acetoamido)-1,4-dimethyluracil, 5-(p-chlorophenoxy-acetamido)-1,3,4-trimethyluracil and 4-amino-5-(p-chlorophenoxy-acetamido)-1,3-dimethyluracil.

According to the invention there are several preparations for the new substituted 5-(phenoxyalkanoylamino)-uracil compounds. These preparations are as follows:

1. Reacting 5-amino-uracil of the formula II

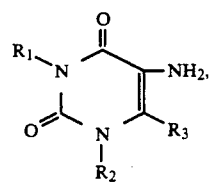

$R_1$, $R_2$ and $R_3$ are as shown above, with substituted phenoxyacetyl chloride or substituted phenoxypropionyl chloride or a reactive ester of a substituted phenoxyacetic acid or phenoxypropionic acid;

The substituted phenoxyacetyl and phenoxypropionyl chlorides have the following formula II'

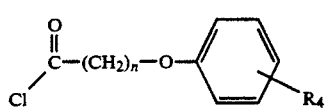

The substituted esters of phenoxyacetic acid or phenoxypropionic acid have the following formula III'

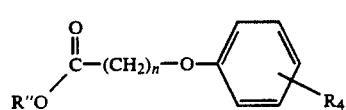

2. Alkylating 5-(Phenoxyalkanoylamino)-uracil of the formula III:

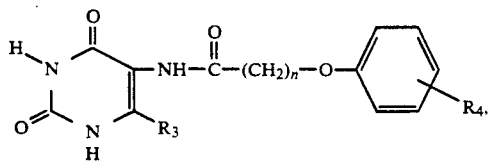 III

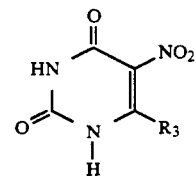 VI where n, $R_3$ and $R_4$ are as described above, in the desired position; and 3. Reacting 5-($\omega$-halogenalkanoylamino-uracils of the formula IV

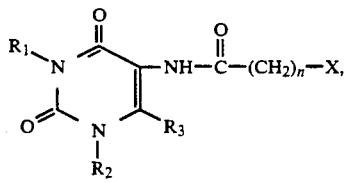 IV where $R_1$, $R_2$ and $R_3$ and n are described above, and X is a chlorine or bromine atom with phenol.

A hydrocarbon such as benzene, toluene or xylene, halogenated aliphatic or aromatic hydrocabons such as dichloromethane, chloroform or chlorobenzene, ethers such as dioxane, esters such as acetic acid ester, ketones, such as acetone, or formamides, such as dimethylformamides can be used as a solvent in the making of the new substituted 5-(phenoxyalkanoylamino)-uracil compounds by the first method indicated with number 1 above.

To speed up the conversion in the case of the first method it is advantageous to use a hydrogen halide acceptor, such as pyridine, triethylamine, N,N-dimethyl aniline or alkali metal hydrogen carbonate and/or alkali metal carbonate.

The reaction temperature can be varied over a wide range. Generally the reaction is performed at the boiling temperature of the solvent being used. The reaction is advantageously performed at 30° to 50° C. in dimethylformamide.

The conversion of 5-amino-uracil of formula II with a reactive ester can occur both in the presence of an inert organic solvent and also in the presence of an excess of the chosen ester. This reaction is advantageously performed at 150° to 200° C.

The starting material for the compound of formula I can be prepared by alkylation, nitration and reduction of the following uracil derivative of the formula V:

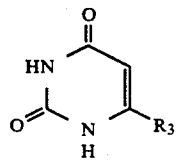 V or from a uracil derivative of the formula VI:

by alkylation and reduction according to known procedures and wherein $R_3$ has the significance as described above.

The new substituted 5-(phenoxyalkanoylamino)-uracil compounds of formula I can be made according to the second method (numbered as method 2 above) in an aqueous or aqueous-organic, advantageously aqueous alcoholic, solvent in the presence of hydrogen halide acceptors, such as alkali metal hydroxide or alkali metal carbonates or in dipolar-aprotic solvents, such as dimethylsulfoxide, in the presence of alkali metal carbonates.

Dialkyl sulfates, alkyl halides, cycloalkyl halides or phenylalkyl halides are suitable as alkylating agents.

This reaction can be performed at reaction temperatures of 20° C. up to boiling temperature of the solvent depending on the alkylating agent.

The new substituted 5-phenoxyalkanoylamino-uracil compounds of formula I can be made according to the third method (numbered as method 3 above) in an aqueous, aqueous-organic or organic solvent in the presence of a hydrogen halide acceptor such as alkali hydroxides or alkali metal carbonates at a reaction temperature of 20° C. up to the boiling temperature of the selected solvent or solvent mixture. The starting material of the formula IV is obtained by reaction of 5-aminouracil of the formula II with chloroacetyl-, bromoacetyl-, chloropropionyl- or bromopropionylhalides in inert organic media in the presence of a hydrogen halide acceptor, as indicated above, according to a known reaction method. Advantageously the reaction is performed at temperatures of 50° to 80° C. in dimethylformamide.

A pharmaceutical composition containing the compounds of formula I is also the subject of the present invention. The composition according to the invention contains at least one compound of the formula I above with another inorganic and organic pharmaceutically acceptable adjuvant substance in a pharmaceutically acceptable carrier, for example in water.

A pharmaceutical composition for treatment of cerebrovascular, neuronal-degenerative and senility-induced disorders associated with learning, memory and cognitive dysfunctions comprises a therapeutically effective amount of a substituted 5-(phenoxyalkanoylamino)-uracil compound of the formula I in a pharmaceutically acceptable carrier.

The pharmaceutical composition according to the invention can be in a variety of suitable forms including tablets, pills, capsules, suppositories, solutions and suspensions with at least one compound of the formula I, with a needed pharmaceutically acceptable adjuvant substance. These pharmaceutical compositions can be made by standard methods available in pharmaceutical practice including mixing, granulation, pill-making and solvation methods. The carriers and/or adjuvant substances are known in current practice and can be, for example, Starch, Stearate, Lactose and so forth.

The new substituted 5-(phenoxyalkanoylamino)-uracil compounds of formula I according to the invention have a strong cerebroprotective action, which makes them suitable as medicines for a variety of cerebral disorders or conditions. They protect the cerebrum from deleterious influences and improve its function. Surprisingly they provide a substantially higher antiamnestic and antihypoxia action than comparable known substances.

Using experimental methods for substances designed to improve the thinking action of the brain, such for example are described in S. Sara and M. David-Remacle in Psycopharmacologia 36 (1974), 59 or W. Hoffmann and A. Rostock, in Pharmazie 38 (1983), 12,869. It was established that the antiamnestic action of a single compound of the formula I was 3 to 100 times stronger than that of Piracetam or 10 to 30 times stronger than that of Meclofenoxate HCl(Table).

The compounds of formula I normalize cerebral function under pathological conditions such those due to chronic alcohol consumption and chronic cerebral minor bleeding. Such pathological factors have a resemblance to human cerebral disorders.

Of special therapeutic significance is the action of the compounds of the invention in protecting the cerebrum from oxygen deficiency, as is the frequent cause of cerebral disfunction. The antihypoxia action is an important criteria for cerebroprotective action of a substance. The compounds of formula I protect mice in an atmosphere having a reduced oxygen concentration prior to death by asphyxiation. The protective action of the compounds of formula I is from 3 to 10 times stronger than that of Piracetam and Meclofenoxate HCl.

The new substituted uracils are free of side effects and are highly compatible.

The $LD_{50}$ as measured in toxicity test in mouse is from 800 to greater than 1700 mg/kg in intraperitoneal application. The results of these toxicity tests on mouse and rat are shown in the following table as well as the effective dosage:

TABLE I

THERAPEUTICALLY EFFECTIVE INTRAPERITONEAL DOSAGES (mg/kg) AND TOXICITY

| Substance of Example: | Antiamnestic Effect-Rat | Antihypoxia Effect-Mouse | $LD_{50}$ mouse |
|---|---|---|---|
| 4 | 100 | 30 | >1700 |
| 2 | 1 | 100 | 800 |
| 3 | 3 | 300 | >1700 |
| 1 | 30 | >300 | >1700 |
| Piracetam | 100 | 300 | >2000 |
| Meclofenoxate HCl | 30 | 300 | 856 |

EXAMPLES

In the following section examples of the compound of formula I and the methods of making those compounds are provided.

EXAMPLE 1

5-(p-Chlorophenoxy-acetamido)-1,4-dimethyluracil 7 g (0.05M) 5-amino-1,4-dimethyluracil is added with stirring to 20.5 g (0.10M) p-chlorophenoxyacetyl chloride in 150 ml of chloroform.

Subsequently 8 ml (0.10M) pyridine is added dropwise, the mixture is stirred for about one hour at 25° to 30° C. and refluxed an additional hour. After cooling, the mixture is stirred with a solution of 17 g potassium carbonate in 200 ml of water. Then a precipitate comes down. This precipitate is filtered with suction, washed with chloroform and dried.

The yield was 7.3 g and the melting point 192°–207° C. with decomposition.

The chloroform phase is separated, agitated with 150 ml water and concentrated to dryness. The residue is taken up in 10 ml isopropanol, filtered by suction and dried. The yield is 4.4 g with a melting point of 185° to 198° C. with decomposition.

The collected solid residues are recrystallized from 44 ml of isopropanol/dimethyl formamide in a ratio of 1:1 with addition of 1 g active charcoal. The crystals formed are filtered with suction, washed with isopropanol and are dried.

The yield was 7.4 g (45.7% theoretical), melting point 202°–211° C. (decomp.)

| $C_{14}H_{14}ClN_3O_4$ Molecular weight 323.7 | | |
|---|---|---|
| Element | % Calculated Theoretically | % Experimentally Determined |
| C | 51.9 | 52.0 |
| H | 4.4 | 4.35 |
| N | 13.0 | 12.9 |

EXAMPLE 2

5-(p-Chlorophenoxy-acetamido)-4-methyluracil 60 g (0.3M) p-chlorophenoxyacetic acid methyl ester, 8.5 g (0.06M) 5-amino-4-methyluracil and 1.5 g ammonium chloride are heated four hours at 200° C. with stirring in a condenser. After cooling to about 50° C. 156 ml 96% ethanol is added and the suspension is stirred from 15 min. Subsequently the precipitate is filtered with suction, washed with ethanol and dried.

The yield was 13.1 g (70.5% of theoretical) and the melting point was 280° to 293° C. (Decomp.).

The raw product is recrystallized from 65 ml dimethylformamide with addition of 1.3 g of activated charcoal. The crystals are filtered with suction washed with dimethyl formamide and acetone and dried at 110° C.

The yield was 5.3 g (28.5% of theoretical) and a melting point of 290°–296° C. (decomp.).

One obtains an additional 3.8 g (20.5% theoretical) by concentration of the mother liquor. The melting point of this additional material is 288° to 293° C. (decomp.).

The total yield amounted to 9.1 g (49.% of theoretical).

| $C_{13}H_{12}ClN_3O_4$ Molecular weight 309.7 | | |
|---|---|---|
| Element | % Calculated Theoretically | % Experimentally Determined |
| C | 50.4 | 50.4 |
| H | 3.9 | 4.0 |
| N | 13.6 | 13.5 |

EXAMPLE 3

5-(p-Chlorophenoxy-acetamido)-1,3,4-trimethyluracil 10.3 g (0.033M) 5-(p-chlorophenoxy-acetamido)-4-methyluracil are dissolved in 70 ml 1N soda liquor with stirring. Subsequently 9.5 ml dimethylsulfate are added dropwise at 30° to 40° C. for two hours, so that the pH of the soda liquor is continuously maintained at pH 9.

After addition of dimethylsulfate the reaction mixture is stirred for an additional hour at 30° to 35° C. The precipitate is filtered with suction, washed with water and dried. The raw product is heated with 100 ml chloroform to boiling and an insoluble residue formed is filtered with suction. The cooled chloroform solution is stirred with 100 ml 1N soda liquor, the chloroform phase is separated and evaporated to dryness. The residue formed is subsequently recrystallized from 2 portions of dimethyl formamide with addition of activated charcoal. The crystals are filtered with suction, washed with 96% ethanol and dried at 80° C.

The total yield amounted to 6 g (53.8.% of theoretical) with a melting point of 206°–209° C.(Decomp).

| | $C_{15}H_{16}ClN_3O_4$ Molecular weight 337.76 | |
|---|---|---|
| Element | % Calculated Theoretically | % Experimentally Determined |
| C | 53.3 | 53.4 |
| H | 4.8 | 4.75 |
| N | 12.4 | 12.4 |

EXAMPLE 4

4-amino-5-(p-Chlorophenoxy-acetamido)-1,3-dimethyluracil 18.8 g 4,5-diamino-1,3-dimethyluracil is added to a solution of 41 g (0.2M) p-chlorophenoxyacetyl chloride in 500 ml chloroform. Subsequently 16 ml (0.2M) pyridine are added with stirring and the mixture is cooled. The mixture is stirred for about one hour at room temperature and under reflux. After initial cooling the mixture the precipitate is filtered with suction, washed twice with 30 ml of chloroform each time and three times with 50 ml ethanol each time. The ethanol moistened product is heated with 400 ml water to boiling. The resulting hot precipitate is filtered with suction washed with hot water and dried.

The raw product is recrystallized from 200 ml dimethylformamide with addition of activated charcoal. The crystals are filtered with suction, washed with dimethyl formamide and ethanol and dried.

The total yield amounted to 27 g (80.% of theoretical) with a melting point of 259°–267° C. (Decomp).

| | $C_{14}H_{15}ClN_4O_4$ Molecular weight 338.7 | |
|---|---|---|
| Element | % Calculated Theoretically | % Experimentally Determined |
| C | 49.6 | 49.55 |
| H | 4.5 | 4.6 |
| N | 16.5 | 16.5 |

EXAMPLE 5

5-(p-Chlorophenoxy-acetamido)-4-methyluracil 82 g( 0.4M) p-chlorophenoxyacetyl chloride in 200 ml toluene is added with stirring to a suspension of 42.2 g (0.3M) 5-amino-4-methyluracil in 400 ml toluene. Subsequently the mixture is heated 7.5 hours under strong reflux. After that most of the toluene is distilled off at normal pressure, the residual toluene is removed azeotropically after addition of 1 liter water. 500 ml ethanol is added to the mixture, and the mixture is heated 30 minutes under reflux. The resulting hot precipitate is filtered by suction to dryness. This product is washed twice with 100 ml portions of hot water and 100 ml ethanol each time and dried at 80° C.

The product is recrystallized from 450 ml dimethyl formamide with addition of activated charcoal. The crystals formed are washed with dimethyl formamide and acetone and dried at 120° C.

The yield was 39.8 g (42.8% of theoretical) and melting point of 288° to 298° C. (decomp.).

EXAMPLE 6

5-(p-Chlorophenoxy-acetamido)-1,3,4-trimethyluracil 5-(p-chlorophenoxy-acetamido)-1,3,4-trimethyluracil, 1.4 g (0.01M) p-chlorophenol, 1.66 g (0.012M) potassium carbonate and 25 ml dimethylformamide are stirred for one hour at 100° C. After addition of 2.45 g (0.01M) 5-chloroacetamido-1,3,4-trimethyluracil, the mixture is heated three hours at 100° to 110° C.

The reaction mixture is cooled to about 30° C. The precipitate formed is filtered to dryness and washed with 10 ml dimethylformamide. The filtrate is subsequently concentrated in vacuum, the residue suspended in 20 ml methanol, filtered to dryness and washed and dried with methanol.

The yield was 2.16 g (63.7% theoretical) and has a melting point of 157° to 208° C. (Decomp.)

The raw product is recrystallized from 110 ml ethanol with addition of 0.2 g activated charcoal. The yield was 1.7 g (50.3% theoretical) with a melting point of 202° to 208° C. (decomp.).

The starting product 5-chloroacetamido-1,3,4-trimethyl uracil can be obtained by the following steps:

To a suspension of 8.5 g (0.05M) 5-amino-1,3,4-trimethyluracil in 50 ml dimethyl formamide one adds 5 ml (0.063M) chloroacetyl chloride dropwise with cooling so that the internal temperature of the mixture does not exceed about 35° C. The mixture is subsequently stirred for 3.5 hours at 30° to 35° C. After that, about 2/3 of the dimethylformamide are vacuum distilled away. The residue is filter by suction, washed with methanol and dried at 80° C. The yield was 7.7 g (62.7% theoretical) with a melting point of 160° to 164° C.

EXAMPLE 7

3-benzyl-5-(p-chlorophenoxyacetamido)-1,4-dimethyluracil 13 g (0.04M) 5-(p-chlorophenoxy-acetamido)-1,4-dimethyluracil, 8.3 g (0.06M) potassium carbonate and 100 ml dimethyl formamide are stirred one hour at 110° C. 7.6 g (0.06M) benzyl chloride is added dropwise and heated 4.5 hours at 110°–120° C. After cooling to room temperature the precipitate is filtered with suction and washed with 10 ml dimethyl formamide. The filtrate is concentrated in vacuum, the residue dissolved in 100 ml toluene and the toluene solution is extracted with 50 ml 1N soda liquor and 50 ml water.

One distills the toluene in vacuo and crystallizes the residue from 42 ml isopropanol with addition of 1 g activated charcoal.

The yield was 11.9 g (71.5% theoretical) at a melting point of 118° to 123° C.

| | $C_{21}H_{20}ClN_3O_4$ Molecular weight 413.8 | |
|---|---|---|
| Element | % Calculated Theoretically | % Experimentally Determined |
| C | 60.9 | 61. |
| H | 4.9 | 4.8 |
| Cl | 8.6 | 8.6 |
| N | 10.15 | 10.15 |

EXAMPLE 8

5-(p-chlorophenoxyacetamido)-uracil 1.87 g (0.01M) p-chlorophenoxyacetic acid is suspended with stirring in 30 ml dry dimethylformamide and dissolved by addition of 1. g (0.01M) triethylamine. The reaction mixture is cooled to 0° to 5° C. internal temperature, mixed with 1.1 g (0.1M) chloroformic acid ethyl ester and stirred one minute at its reaction temperature. To the reaction mixture of the mixed anhydrides one rapidly adds a solution of 1.27 g (0.01M) 5-aminouracil in dry dimethylformamide and stirs for 30 minutes. Subsequently the reaction mixture is poured into 1 liter ice water, the precipitate is filtered with suction, dried and recrystallized from water in the ratio 1:1.

The yield was 2.3 g (78% of theoretical) and has a melting point greater than 300° C. (Decomp.).

| | $C_{12}H_{10}ClN_3O_4$ Molecular weight 295.7 | |
|---|---|---|
| Element | % Calculated Theoretically | % Experimentally Determined |
| C | 48.74 | 48.62 |
| H | 3.41 | 3.59 |
| Cl | 11.99 | 11.98 |
| N | 14.21 | 14.27 |

EXAMPLE 9

4-methyl-5-(p-methoxyphenoxy-acetamido)-uracil 1.82 g (0.01M) p-methoxyphenoxyacetic acid and 1.41 g (0.01M) 5-amino-4-methyl uracil are reacted similar to the method of example 8. The solvent was DMF:H₂O in ratio 1:2.

The yield amounted to 2.3 g (75.% of theoretical) with a melting point of 282°-284° C.

| | $C_{14}H_{15}N_3O_5$ Molecular weight 305.3 | |
|---|---|---|
| Element | % Calculated Theoretically | % Experimentally Determined |
| C | 55.9 | 54.95 |
| H | 4.95 | 5.33 |
| N | 13.76 | 13.12 |

EXAMPLE 10

4-methyl-5-(p-methylphenoxyacetamido)-uracil

This compound is made from 1.66 g (0.01M) p-methyl-phenoxyacetic acid and 1.41 g (0.01M) 5-amino-4-methyl uracil in a manner similar to Example 8. The solvent was DMF:H₂O in ratio 1:2.

The yield amounted to 2.2 g (76.% of theoretical) with a melting point of 298°-300° C.

| | $C_{14}H_{15}N_3O_4$ Molecular weight 289.3 | |
|---|---|---|
| Element | % Calculated Theoretically | % Experimentally Determined |
| C | 58.12 | 58.18 |
| H | 5.23 | 5.24 |
| N | 14.53 | 14.68 |

EXAMPLE 11

5-(o-chlorophenoxyacetamido)-4-methyluracil

This compound is made from 1.87 g (0.01M) o-chlorophenoxyacetic acid and 1.41 g (0.01M) 5-amino-4-methyl uracil in a manner similar to Example 8. The solvent was DMF:H₂O in ratio 1:2.

The yield amounted to 2.2 g (71.% of theoretical) with a melting point of 355°-357° C.

| | $C_{13}H_{12}ClN_3O_4$ Molecular weight 309.2 | |
|---|---|---|
| Element | % Calculated Theoretically | % Experimentally Determined |
| C | 50.4 | 50.4 |
| H | 3.9 | 3.9 |
| Cl | 11.45 | 11.3 |
| N | 13.6 | 13.7 |

EXAMPLE 12

5-(p-chlorophenoxy-β-propionamido)-4-methyluracil

This compound is made from 2.0 g (0.01M) p-chlorophenoxy-β-propionic acid and 1.41 g (0.01M) 5-amino-4-methyl uracil in a manner similar to Example 8. The solvent was DMF:H₂O in ratio 1:1.

The yield amounted to 2.25 g (70.% of theoretical) with a melting point of 235°-238° C.

| | $C_{14}H_{14}ClN_3O_4$ Molecular weight 323.7 | |
|---|---|---|
| Element | % Calculated Theoretically | % Experimentally Determined |
| C | 51.94 | 51.99 |
| H | 4.36 | 4.39 |
| Cl | 10.95 | 10.9 |
| N | 12.98 | 12.99 |

EXAMPLE 13

5-(p-chlorophenoxy-β-propionamido)-1,3,4-trimethyluracil

This compound is made from 2.0 g (0.01M) p-chlorophenoxy-β-propionic acid and 1.71 g (0.01M) 5-amino-1,3,4-trimethyluracil in a manner similar to Example 8. The solvent was ethanol.

The yield amounted to 1.4 g (40.% of theoretical) with a melting point of 187°-190° C.

| | $C_{16}H_{18}ClN_3O_4$ Molecular weight 351.8 | |
|---|---|---|
| Element | % Calculated Theoretically | % Experimentally Determined |
| C | 54.63 | 53.97 |
| H | 5.16 | 5.08 |
| Cl | 10.08 | 10.11 |
| N | 11.94 | 11.99 |

EXAMPLE 14

5-(p-chlorophenoxy-β-propionamido)-uracil hydrate

This compound is made from 2.0 g (0.01M) p-chlorophenoxy-β-propionic acid and 1.27 g (0.01M) 5-amino uracil in a manner similar to Example 8. The solvent was DMF:H₂O in ratio 1:1.

The yield amounted to 2.3 g (70.% of theoretical) with a melting point of 275°-278° C.

| C$_{13}$H$_{12}$ClN$_3$O.H$_2$O Molecular weight 327.7 | | |
|---|---|---|
| Element | % Calculated Theoretically | % Experimentally Determined |
| C | 47.64 | 47.68 |
| H | 4.31 | 4.36 |
| Cl | 10.82 | 10.76 |
| N | 12.82 | 12.76 |

EXAMPLE 15

5-(p-chlorophenoxyacetamido)-3,4-dimethyluracil 12.4 g (0.04M) 5-(p-chlorophenoxyacetamido)-4-methyluracil are dissolved in 16.3 g (0.08M) bis-trimethylsilylacetamide at a bath temperature of 120° to 130° C. After that 20.2 g (0.16M) dimethyl sulfate are added so that the reaction solution boils. The reaction solution is left for 2 minutes at a bath temperature of 120° to 140° C. After cooling 550 ml water was added to the reaction mixture. The precipitate is filtered by suction, washed with water and a little methanol, dried and recrystallized from i-propanol/water in the ratio of 1:1.

The yield amounted to 1.8 g (57.% of theoretical) with a melting point of 267°-272° C.

| C$_{14}$H$_{14}$ClN$_3$O$_4$ Molecular weight 323.7 | | |
|---|---|---|
| Element | % Calculated Theoretically | % Experimentally Determined |
| C | 51.94 | 51.76 |
| H | 4.36 | 4.38 |
| Cl | 10.95 | 10.75 |
| N | 12.98 | 12.99 |

While the invention has been illustrated and embodied in substituted 5-(phenoxyalkanoylamino)-uracil compounds, methods of making same and pharmaceutical compositions based one same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

We claim:

1. A substituted 5-(phenoxyalkanoylamino)uracil compound having the following formula I:

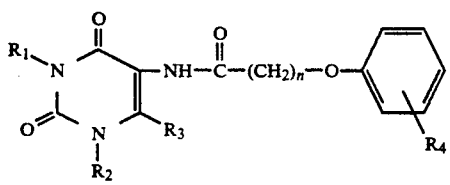

wherein R$_1$ and R$_2$ are each independently selected from the group consisting of hydrogen; branched and linear, unsubstituted, oxo-substituted and hydroxy-substituted alkyl groups having 1 to 6 carbon atoms; branched and straight chain, unsubstituted, oxo-substituted and hydroxy-substituted alkenyl and alkynyl groups having 1 to 6 carbons atoms; cycloalkyl groups having from 3 to 7 carbon atoms and cycloalkylmethyl groups having a cycloalkyl residue having from 3 to 7 carbon atoms; and phenylalkyl groups, each of said phenylalkyl groups having an alkyl residue having from 1 to 3 carbon atoms and a phenyl residue, the phenyl residue being unsubstituted or having a substituent selected from the group consisting of halogen, methoxy, methyl and trifluoromethyl groups;

R$_3$ is selected from the group consisting of hydrogen, methyl and amino groups;

R$_4$ is selected from the group consisting of halogen, methoxy and methyl groups, and n is 1 or 2.

2. A substituted 5-(phenoxyalkanoylamino)-uracil compound selected from the group consisting of
5-(p-chlorophenoxy-acetoamido)-1,4-dimethyluracil,
5-(p-chlorophenoxy-acetamido)-3,4-dimethyluracil,
5-(p-chlorophenoxy-acetamido)-1,3,4-trimethyluracil,
5-(p-chlorophenoxy-acetamido)-uracil,
3-benzyl-5-(p-chlorophenoxy-acetamido)-1,4-dimethyluracil, 4-methyl-5-(p-methoxyphenoxy-acetamido)-uracil, 4-methyl-5-(p-methylphenoxy-acetamido)-uracil, 5-(p-chlorophenoxy-acetamido)-4-methyluracil, 5-(p-chlorophenoxy-$\beta$-propionamido)-4-methyluracil, 5-(p-chlorophenoxy-$\beta$-propionamido)-1,3,4-trimethyluracil, 5-(p-chlorophenoxy-$\beta$-propionamido)-uracil hydrate, 5-(p-chlorophenoxy-acetamido)-4-methyluracil and 4-amino-5-(p-chlorophenoxy-acetamido)-1,3-dimethyluracil.

3. A substituted 5-(phenoxyalkanoylamino)-uracil compound as defined in claim 2 selected from the group consisting of 5-(p-chlorophenoxy-acetoamido)-1,4-dimethyluracil, 5-(p-chlorophenoxy-acetamido)-1,3,4-trimethyluracil and 4-amino-5-(p-chlorophenoxy-acetamido)-1,3-dimethyluracil.

4. An antiamnestic and antihypoxic pharmaceutical composition containing, in a pharmaceutically acceptable carrier, a therapeutically effective amount of a substituted 5-(phenoxyalkanoylamino)-uracil compound having the following formula I:

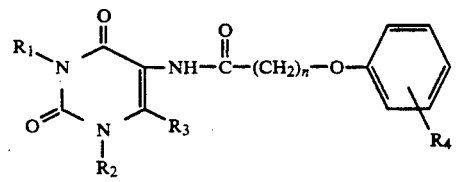

wherein

R$_1$ and R$_2$ are each independently selected from the group consisting of hydrogen; branched and linear, unsubstituted, oxo-substituted and hydroxy-substituted alkyl groups having 1 to 6 carbon atoms; branched and linear, unsubstituted, oxo-substituted and hydroxy-substituted alkenyl and alkynyl groups having 1 to 6 carbons atoms; cycloalkyl groups having from 3 to 7 carbon atoms and cycloalkylmethyl groups having a cycloalkyl residue having from 3 to 7 carbon atoms; and phenylalkyl groups, each of said phenylalkyl groups having an alkyl residue having from 1 to 3 carbon atoms and a phenyl residue, the phenyl residue being unsubstituted or having a substituent selected from the group consisting of halogen, methoxy, methyl and trifluoromethyl groups;

$R_3$ is selected from the group consisting of hydrogen, methyl and amino groups;

$R_4$ is selected from the group consisting of halogen, methoxy and methyl groups, and n is 1 or 2.

5. An antiamnestic and antihypoxic pharmaceutical composition containing, in a pharmaceutically acceptable carrier, a therapeutically effective amount of a substituted 5-(phenoxyalkanoylamino)-uracil compound selected from the group consisting of 5-(p-chlorophenoxy-acetoamido)-1,4-dimethyluracil,
5-(p-chlorophenoxy-acetamido)-3,4-dimethyluracil,
5-(p-chlorophenoxy-acetamido)-1,3,4-trimethyluracil,
5-(p-chlorophenoxy-acetamido)-uracil,
3-benzyl-5-(p-chlorophenoxy-acetamido)-1,4-dimethyluracil, 4-methyl-5-(p-methoxyphenoxy-acetamido)-uracil, 4-methyl-5-(p-methylphenoxy-acetamido)-uracil, 5-(p-chlorophenoxy-acetamido)-4-methyluracil, 5-(p-chlorophenoxy-$\beta$-propionamido)-4-methyluracil, 5-(p-chlorophenoxy-$\beta$-propionamido)-1,3,4-trimethyluracil, 5-(p-chlorophenoxy-$\beta$-propionamido)-uracil hydrate, 5-(p-chlorophenoxy-acetamido)-4-methyluracil and 4-amino-5-(p-chlorophenoxy-acetamido)-1,3-dimethyluracil.

6. An antiamnestic and antihypoxic pharmaceutical composition as defined in claim 5, wherein the substituted 5-phenoxyalkanoylamino)-uracil compound is selected from the group consisting of 5-(p-chlorophenoxy-acetoamido)-1,4-dimethyluracil,
5-(p-chlorophenoxy-acetamido)-1,3,4-trimethyluracil and
4-amino-5-(p-chlorophenoxy-acetamido)-1,3-dimethyluracil.

7. Method of treating cerebrovascular, neuronal-degenerative and senility-induced disorders associated with learning, memory and cognitive dysfunctions of patients comprising administering the pharmaceutical composition as defined in claim 4.

8. Method of treating cerebrovascular, neuronal-degenerative and senility-induced disorders associated with learning, memory and cognitive dysfunctions of patients comprising administering the pharmaceutical compositions as defined in claim 5.

9. A substituted 5-(phenoxyalkanoylamino)-uracil compound having the following formula I:

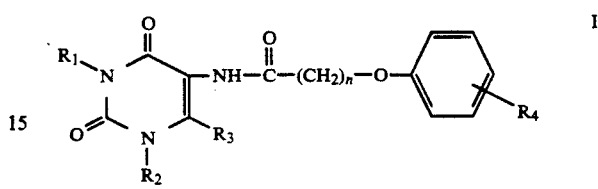

wherein $R_1$ and $R_2$ are each independently selected from the group consisting of hydrogen; branched and linear alkyl groups having 1 to 6 carbon atoms; branched and straight chain alkenyl and alkynyl groups having 1 to 6 carbons atoms; cycloalkyl groups having from 3 to 7 carbon atoms and cycloalkylmethyl groups having from 3 to 7 carbon atoms; and phenylalkyl groups, each of said phenylalkyl groups having an alkyl residue having from 1 to 3 carbon atoms and a phenyl residue, the phenyl residue being unsubstituted or having a substituent selected from the group consisting of halogen, methoxy, methyl and trifluoromethyl groups;

$R_3$ is selected from the group consisting of hydrogen, methyl and amino groups;

$R_4$ is selected from the group consisting of halogen, methoxy and methyl groups, and n is 1 or 2.

* * * * *